United States Patent [19]

Sugihara et al.

[11] Patent Number: 4,697,027

[45] Date of Patent: Sep. 29, 1987

[54] METHOD FOR PURIFYING ALKOXYSILANE

[75] Inventors: Junpei Sugihara; Takeshi Imai; Shuzo Toida; Ikuzo Takahashi, all of Chiba, Japan

[73] Assignee: Toray Silicon Co., Ltd., Tokyo, Japan

[21] Appl. No.: 923,378

[22] Filed: Oct. 27, 1986

[30] Foreign Application Priority Data

Nov. 14, 1985 [JP] Japan ................................. 60-255469

[51] Int. Cl.$^4$ ............................. C07F 7/08; C07F 7/18
[52] U.S. Cl. ..................................... 556/466; 556/415; 556/416; 556/417; 556/446; 556/482; 556/483; 556/485; 556/488; 556/489
[58] Field of Search ............... 556/466, 415, 416, 417, 556/446

[56] References Cited

U.S. PATENT DOCUMENTS 4,127,598 11/1978 Micentee ........................ 556/466 X
4,156,689 5/1979 Ashby et al. .................... 556/466 X

FOREIGN PATENT DOCUMENTS 48-97070 8/1973 Japan ................................... 556/466
60-252488 12/1985 Japan ................................... 556/466
1115052 5/1968 United Kingdom ................. 556/466
852874 8/1981 U.S.S.R. .............................. 556/466

OTHER PUBLICATIONS

Chung and Hayes, J. of Organometallic Chemistry, 265 (1984), pp. 135–139.

*Primary Examiner*—Paul F. Shaver
*Attorney, Agent, or Firm*—Carl A. Yorimoto

[57] ABSTRACT

A method for purifying alkoxysilane with the general formula, $R_mSi(OR^1)_{4-m}$. The method significantly lowers the level of non-hydrolyzable chlorine-based impurities, as well as the level of hydrolyzable chlorine-based impurities. The method comprises: (i) heating the alkoxysilane in the presence of a treating agent selected from a group which consists of acid clays and metal halides; (ii) contacting the alkoxysilane with a neutralization agent; and (iii) separating the alkoxysilane from the unused neutralization agent and by-products of neutralization.

14 Claims, No Drawings

METHOD FOR PURIFYING ALKOXYSILANE

BACKGROUND OF THE INVENTION

This invention relates to a method for purifying alkoxysilanes which contain chlorine-based impurities. More specifically, the present invention relates to a method for purifying crude alkoxysilanes in which the total chlorine-based impurities are reduced to extremely low levels in the final purified alkoxysilanes.

Alkoxysilanes have recently found increasing application in electric and electronic fields; however, alkoxysilane purity must be extremely high in these applications. Due to this need for higher purity, the development of a purification method that affords a very pure alkoxysilane is a matter of some urgency.

Alkoxysilanes with the general formula $R_mSi(OR^1)_{4-m}$ are produced by the liquid-phase or vapor-phase catalytic reaction of the corresponding chlorosilane with alcohol. The crude alkoxysilane product of this reaction contains hydrolyzable and non-hydrolyzable chlorine-based impurities. The crude alkoxysilane product containing such chlorine-based impurities has heretofore been purified by neutralization with a neutralization agent followed by distillation to separate the alkoxysilane from non-volatiles such as the neutralization salts. However, in this method, impurities based on non-hydrolyzable chlorine such as carbon-bonded chlorine, for example, chloromethyltrimethoxysilane, cannot be removed. Only hydrochloric acid and impurities based upon hydrolyzable chlorine, such as chlorosilane, etc., can form neutralization salts using any of anhydrous ammonia, amines, or basic compounds which contain metal, such as sodium, potassium or magnesium, etc., as the neutralization agent.

Chung and Hayes in *Journal of Organometallic Chemistry*, 265 (1984), pp.135-139, describe a method for the removal of impurities based upon non-hydrolyzable chlorine from alkoxysilanes. In the method of Chung and Hayes, alkoxysilane containing approximately 400 parts per million non-hydrolyzable chlorine is heated in the presence of either lithium aluminum hydride, tetramethylguanidine, magnesium oxide, dibutyltin dihydride or metallic sodium and then distilled. However, the problem with this method is that non-hydrolyzable chlorine present as an impurity in the alkoxysilane can be removed to less than 100 ppm only using metallic sodium. However, while the use of metallic sodium will give less than 100 ppm non-hydrolyzable chlorine in the alkoxysilane, the handling of metallic sodium poses a significant safety hazard for industrial operations.

As discussed above, prior purification methods suffer from problems in the removal of chlorine-based impurities. The objective of the present invention is to provide alkoxysilane which contains very low levels of chlorine-based impurities and, in particular, which has a low electrical conductivity, thus being useful in the electric and electronic fields, by virtue of a relatively simple method for freeing alkoxysilane of both hydrolyzable chlorine-based impurities and non-hydrolyzable chlorine-based impurities.

The method for purifying alkoxysilane according to the instant invention removes both hydrolyzable chlorine-based impurities and non-hydrolyzable chlorine-based impurities from alkoxysilane containing chlorine-based impurities by heating in the presence of acid clay or metal halide. Due to this novel feature, an alkoxysilane is readily produced which will contain extremely low chlorine-based impurity levels, levels not easily and simply attained by prior methods, and which will have a low electrical conductivity. Accordingly, it is quite useful in applications in electric and electronic fields, where a very pure and low-conductivity alkoxysilane is required, as well as in other prior applications of alkoxysilanes.

DESCRIPTION OF THE INVENTION

In accordance with the instant invention there is provided a method for purifying alkoxysilane with the general formula, $R_mSi(OR^1)_{4-m}$, under conditions that will be delineated herein. What is described, therefore, is a method for purifying an alkoxysilane having the general formula $$R_mSi(OR^1)_{4-m}$$

wherein R is a hydrogen atom, $C_{1-8}$ substituted or unsubstituted monovalent hydrocarbon group; $R^1$ is a $C_{1-8}$ substituted or unsubstituted monovalent hydrocarbon group; and m is an integer having a value of 0, 1, 2, or 3, the method comprising:

(i) heating the alkoxysilane in the presence of a treating agent selected from a group which consists of acid clays and metal halides;

(ii) contacting the alkoxysilane with a neutralization agent; and (iii) separating the alkoxysilane from the treating agent, the unused neturalization agent, and the by-products of neutralization.

The method of the instant invention for purifying alkoxysilane which contains chlorine-based impurities can be applied to the crude alkoxysilane produced by chlorosilane alkoxylation, as well as to alkoxysilane for which hydrolyzable chlorine-based impurities have been neutralized and removed but which still contains non-hydrolyzable chlorine-based impurities. A crude alkoxysilane which contains large amounts of impurities such as unreacted alcohol is preferably distilled in order to remove the unreacted alcohol before being purified by the instant invention.

Steps (i), (ii) and (iii) must be conducted in this order in the purification method of the instant invention. This is due to the fact that a neutralization step and a step for removing the salts of neutralization must both be conducted after the execution of step (i).

Alkoxysilane which may be purified by the instant invention has the general formula, $$R_mSi(OR^1)_{4-m},$$

as defined, supra. R is a hydrogen atom or $C_{1-8}$ substituted or unsubstituted monovalent hydrocarbon group, $R^1$ is a $C_{1-8}$ substituted or unsubstituted monovalent hydrocarbon groups, for which specific examples are alkyl groups such as methyl, ethyl, propyl and octyl; alkenyl groups such as vinyl and allyl; aryl groups such as phenyl, tolyl and xylyl; aralkyl groups such as benzyl and these groups in which part or all of the hydrogen atoms of the monovalent hydrocarbon group have been substituted by cyano groups or halogen atoms. In addition $R^1$ may be an alkoxyalkyl group.

Specific examples of said alkoxysilanes are trimethoxysilane, triethoxysilane, tetramethoxysilane, tetraethoxysilane, methyldimethoxysilane, methyldiethoxysilane, trimethylmethoxysilane, trimethoxyethoxysilane, methyltrimethoxysilane, methyltriethoxysilane, tris-2-methoxyethoxysilane, vinylmethyldiethoxysilane, vinyltrimethoxysilane, vinyltriethoxysilane, vinyltri-2-methoxyethoxysilane, phenyltrimethoxysilane, diphenylmethoxysilane, phenylmethyldimethoxysilane and allyltrimethoxysilane.

The mechanism by which the acid clay or metal halide used in step (i) of the instant invention interacts with non-hydrolyzable chlorine is not clear; however, it is believed by the inventors that the heat treatment with acid clay o metal halide has a catalytic effect and converts non-hydrolyzable chlorine into hydrolyzable chlorine. The acid clay used in step (i) may be a naturally occurring acid clay which may be used as such or a so-called activated clay, which has been treated with acid. Specific but non-limiting examples of acid-treated activated clays are K-500 from Nippon Kassei Hakudo Co., Ltd., Tonsil FF from Sued-Chemie AG of West Germany and Filtrol 20LM from the Filtrol Corp. of the United States.

The metal halide used in step (i) may be the halide of a metal from Groups II to VI of the Periodic Table; however, it is not limited to this set. Specific examples of the metal halides are iron chloride, copper chloride, nickel chloride, zinc chloride, cobalt chloride, manganese chloride, chromium chloride, molybdenum chloride and cerium chloride and the iodides, bromides and fluorides of these metals.

The acid clay or metal halide is generally used at a concentration of equal to or greater than 0.01 weight percent based on the weight of the alkoxysilane subjected to heating in order to remove the chlorine-based impurities effectively. Increasing the quantity of acid clay or metal halide used will reduce the heating time, but economic considerations lead to the use generally of 0.05 to 2 weight percent acid clay or metal halide based on the weight of alkoxysilane to be treated.

The heating temperature in step (i) is generally in the range of 50° to 200° C. When the alkoxysilane to be heated has a boiling point below 200° C., it is desirably heated at its boiling point with reflux.

The reaction time will vary depending on the amount of impurity present in the alkoxysilane subjected to heating, on the quantity of addition of acid clay or metal halide and on the reaction temperature. Reaction time is generally in the range of 30 minutes to 10 hours.

The treating agent does not need to be removed prior to contacting the alkoxysilane with a neutralization agent. However, removal of the treating agent prior to contacting the alkoxysilane with a neutralization agent can have the impact of reducing the amount of neutralization agent needed. Removal of the treating agent can be effected by known means for removing solids from liquids such as filtration or the like.

The neutralization agent used in step (ii) of the instant invention acts to neutralize acidic compounds collaterally produced from the metal halide or acid clay and the hydrolyzable chlorine produced in process (i), so neutralization agents known in the art can be used. The neutralization agent can be any of those selected from a group which consists of anhydrous ammonia; amines; basic compounds which contain metals such as sodium, potassium, calcium and magnesium; alkylene oxides and orthoesters.

The amines are exemplified by tertiary amines, secondary amines and primary amines such as triethylamine, tributylamine, trioctylamine, N,N-dimethyldodecylamine, diethylamine, dibutylamine, propylamine, butylamine, octylamine, stearylamine, aniline, pyridine, diphenylamine, quinoline, ethanolamine, diethanolamine and triethanolamine.

The basic compounds which contain metals can be those selected from a group which includes sodium hydroxide, potassium hydroxide, magnesium hydroxide, sodium methylate, magnesium oxide, sodium carbonate and magnesium carbonate.

Specific examples of the alkylene oxides are ethylene oxide, propylene oxide, and butylene oxide; and concrete examples of the orthoesters are trimethyl orthoformate and triethyl orthoacetate.

The quantity of use of neutralization agent is generally equal to or less than 1.0 weight percent, based on the weight of alkoxysilane used.

The neutralization salt produced by neutralization in step (ii) is removed in step (iii) of the instant invention by known means of separating a liquid from a solid. Examples of such means for separating a liquid from a solid are: (1) dissolving of the salt of neutralization with water and separation of the water and dissolved solid from the alkoxysilane; (2) removal of the solid salt of neutralization by filtration; or (3) distillation of the alkoxysilane from the solid salt of neutralization. A combination of these means for separating may be used in order to remove the salt of neutralization effectively.

PREFERRED EMBODIMENT OF THE INVENTION

The preferred mode of carrying out the instant invention is to use an acid-treated activated clay or a metal chloride in the heat treatment of step (i). The metal chloride is preferably a chloride of a metal from Groups II to VI of the Periodic Table. The acid-treated activated clay or metal chloride is preferably used at a concentration in the range of 0.05 to 1.0 weight percent, based upon the weight of the alkoxysilane.

The temperature of the heat treatment of step (i) is preferably the boiling point of the alkoxysilane. The preferred time for the heat treatment is in the range of 1 to 5 hours.

The preferred neutralization agent is selected from a group which consists of basic compounds which contain metals. The preferred concentration of the neutralization agent is less than or equal to 0.5 weight percent, based upon the weight of the alkoxysilane.

The preferred method of removing the salt of neutralization from the treated alkoxysilane is filtration of the solids away from the alkoxysilanes or distillation of the alkoxysilanes from the salt of neutralization.

The following examples are presented to be illustrative of the instant invention and are not to be construed as limiting the instant invention as delineated in the claims.

EXAMPLE 1

Methyltrichlorosilane is methoxylated by a batch method followed by neutralization with sodium methylate and removal of the neutralization salt by filtration. A purified methyltrimethoxysilane with the following properties is obtained by distillation: purity=99.8 weight percent (%) by gas chromatography; total chlorine=81 parts per million (ppm) by elemental analysis; electrical conductivity of the 2 weight percent (%) aqueous solution=17.0 microsiemens/cm; pH=4.5.

200 grams (g.) of this methyltrimethoxysilane is placed in a 300 milliliter (ml.) flask equipped with a condenser, thermometer and stirring motor. Acid clay (K-500 from Nippon Kassei Hakudo Co., Ltd.) is added at 500 ppm based on the methyltrimethoxysilane, and this mixture is then heated at 100°±2° C. under reflux for 2 hours. The acid clay is then removed by filtration. The obtained mixture is neutralized with 0.5 g. potassium hydroxide and then washed with ion-exchanged water in order to remove the neutralization salt. This purified methyltrimethoxysilane contains 6 ppm total chlorine; the 2% aqueous solution has an electrical conductivity of 1.67 microsiemens/cm and the pH is 5.43.

In a comparison example, the methyltrimethoxysilane is treated exactly as above, with the exception that it is not heated in the presence of acid clay. The total chlorine is 78 ppm, the 2% aqueous solution has an electrical conductivity of 16.5 microsiemens/cm and the pH is 4.9.

EXAMPLE 2

Methyltrichlorosilane is continuously brought into counter-current contact with methanol vapor in a packed column. The crude methyltrimethoxysilane product has the following properties: methanol content=16.5% by gas chromatographic analysis; hydrolyzable chlorine=760 ppm by silver nitrate titration after neutralization with sodium methylate; total chlorine=1,000 ppm; electrical conductivity of the 2% aqueous solution=194 microsiemens/cm.

57.8 g. of this crude methyltrimethoxysilane is heated in a 100 ml. flask in order to remove the major portion of the methanol; and ferric chloride is then added at 400 ppm based on the crude methyltrimethoxysilane. This is then heated at 91° C. under reflux for 1 hour. After neutralization with sodium methylate, the methyltrimethoxysilane is distilled by simple distillation. The methyltrimethoxysilane product has no trace of hydrolyzable chlorine and the total chlorine content is 12 ppm. The 2% aqueous solution has an electrical conductivity of 1.6 microsiemens/cm.

For a comparison example, the methyltrimethoxysilane is treated exactly as above in Example 2, with the exception that it is not heated in the presence of ferric chloride. The total chlorine content is then 248 ppm and the 2% aqueous solution has an electrical conductivity of 45 microsiemens/cm.

EXAMPLE 3

The methyltrimethoxysilane is purified by the method described in Example 2 with the exception that zinc chloride is added at 1% based on the crude methyltrimethoxysilane, instead of the ferric chloride used in Example 2, and heating is conducted at 90° to 95° C. under reflux for 1 hour. The hydrolyzable chlorine content is then 10 ppm, the total chlorine content is 59 ppm and the 2% aqueous solution has an electrical conductivity of 2.1 microsiemens/cm.

EXAMPLE 4

The methyltrimethoxysilane is purified by the method described in Example 2 with the exception that cerium chloride is added at 1% based on the crude methyltrimethoxysilane, instead of the ferric chloride used in Example 2, and heating is conducted at 90° to 95° C. under reflux for 1.5 hours. The total chlorine content is then 40 ppm and the 2% aqueous solution has an electrical conductivity of 2.2 microsiemens/cm.

EXAMPLE 5

The methyltrimethoxysilane is purified by the method described in Example 2 with the exception that ferric bromide is added at 1% based on crude methyltrimethoxysilane, instead of the ferric chloride used in Example 2, and heating is conducted at 90° to 95° C. under reflux for 2 hours. The results are a total chlorine content of 48 ppm and an electrical conductivity of 4.5 microsiemens/cm.

EXAMPLE 6

Tetraethoxysilane produced by the ethoxylation of tetrachlorosilane and then purified by a prior method has a total chlorine content of 64 ppm and an electrical conductivity of 8.5 microsiemens/cm.

200 g. of this tetraethoxysilane is placed in a flask, 500 ppm acid clay (Filtrol 20LM from the Filtrol Corp.) is added and this is heated under reflux for 1 hour and then worked up by the method of Example 1. The resulting tetraethoxysilane has a total chlorine content of 4 ppm and an electrical conductivity of 1.0 microsiemens/cm.

That which is claimed is:

1. A method for purifying an alkoxysilane having the general formula

wherein R is a hydrogen atom, $C_{1-8}$ substituted or unsubstituted monovalent hydrocarbon group; $R^1$ is a $C_{1-8}$ substituted or unsubstituted monovalent hydrocarbon group; and m is an integer having a value of 0, 1, 2, or 3, the method comprising:
   (i) heating the alkoxysilane in the presence of a treating agent selected from a group which consists of acid clays and metal halides;
   (ii) contacting the alkoxysilane with a neutralization agent; and
   (iii) separating the alkoxysilane from treating agent, the unused neutralization agent and the by-products of neutralization.

2. The method according to claim 1, wherein the method further comprises removing the treating agent after (i) and before (ii).

3. The method according to claim 1, wherein the treating agent is an acid clay.

4. The method according to claim 3, wherein the acid clay is selected from a group which consists of naturally-occurring acid clays and acid-treated activated clays.

5. The method according to claim 4, wherein the acid clay is an acid-treated activated clay.

6. The method according to claim 1, wherein the treating agent is a metal halide.

7. The method according to claim 6, wherein the metal halide is selected from a group which consists of halides of metals of Groups II and VI of the Periodic Table.

8. The method according to claim 7, wherein the metal halide is a metal chloride.

9. The method according to claim 1, wherein the treating agent is used at a concentration of greater than 0.01 weight percent, based upon the weight of the alkoxysilane.

10. The method according to claim 9, wherein the treating agent is used at a concentration in the range of 0.05 to 2.0 weight percent, based upon the weight of the alkoxysilane.

11. The method according to claim 1, wherein the neutralization agent is selected from a group which consists of ammonia, amines, basic compounds which contain metals, alkylene oxides and orthoesters.

12. The method according to claim 11, wherein the basic compounds which contain metals are selected from a group which consists of sodium hydroxide, potassium hydroxide, magnesium hydroxide, sodium methylate, magnesium oxide, sodium carbonate, and magnesium carbonate.

13. The method according to claim 1, wherein the neutralization agent is present at a concentration of less than 1.0 weight percent, based upon the weight of the alkoxysilane.

14. The method according to claim 13, wherein the neutralization agent is present at a concentration of less than 0.5 weight percent, based upon the weight of the alkoxysilane.

* * * * *